United States Patent [19]
Angelchik

[11] Patent Number: 5,381,800
[45] Date of Patent: Jan. 17, 1995

[54] METHOD FOR TESTING FOR ESOPHAGITIS

[76] Inventor: Jean P. Angelchik, 522 W. Northview, Phoenix, Ariz. 85021

[21] Appl. No.: 850,985

[22] Filed: Mar. 12, 1992

[51] Int. Cl.⁶ .............................................. A61B 5/103
[52] U.S. Cl. .................................. 128/780; 128/898
[58] Field of Search ............... 128/670, 695, 898, 774, 128/780, 897, 898; 604/890.1, 27, 28, 36, 49, 54, 77, 80, 93, 117, 131, 181, 185, 244, 245, 148, 200, 212; 222/92, 107; 206/363, 364, 438

[56] References Cited

U.S. PATENT DOCUMENTS

| | | | |
|---|---|---|---|
| 598,407 | 2/1898 | Armstrong | 604/36 |
| 1,911,671 | 5/1933 | Blauvelt | 604/244 |
| 2,335,799 | 11/1943 | Schwab | 604/244 |
| 3,480,003 | 11/1969 | Crites | 128/748 |
| 4,168,703 | 9/1979 | Kenigsberg | 128/748 |
| 4,214,593 | 7/1980 | Imbruce et al. | 128/748 |
| 4,747,827 | 5/1988 | Micek | 604/54 |
| 4,773,394 | 9/1988 | Reichstein et al. | 128/4 |
| 4,840,614 | 6/1989 | Maaz | 604/53 |
| 5,084,022 | 1/1992 | Claude | 604/164 |

Primary Examiner—Stephen C. Pellegrino
Assistant Examiner—Guy V. Tucker
Attorney, Agent, or Firm—Tod R. Nissle

[57] ABSTRACT

A method and apparatus for administering a test to detect the esophagitis in a patient utilizes a sealed pliable tube. When the tube is unsealed and inserted in the esophagus of a patient, an acidic solution stored in the tube flows into the esophagus and, if the patient has esophagitis, causes the chest pain or other symptoms which the patient experiences during esophagitis.

7 Claims, 2 Drawing Sheets

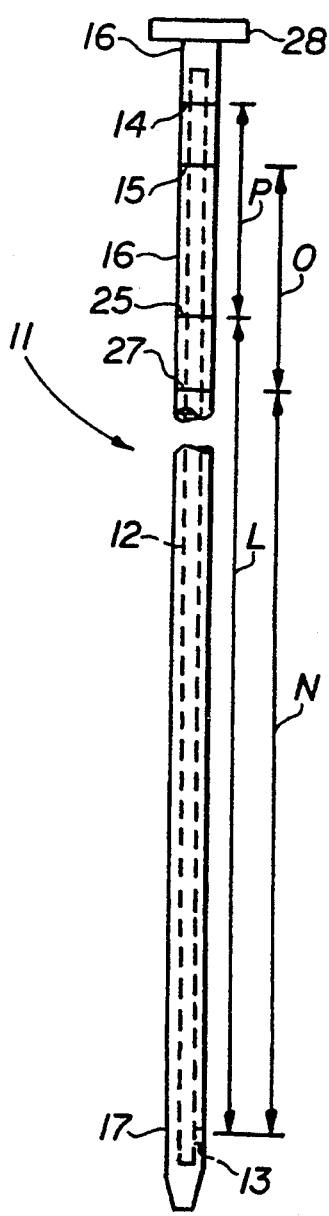
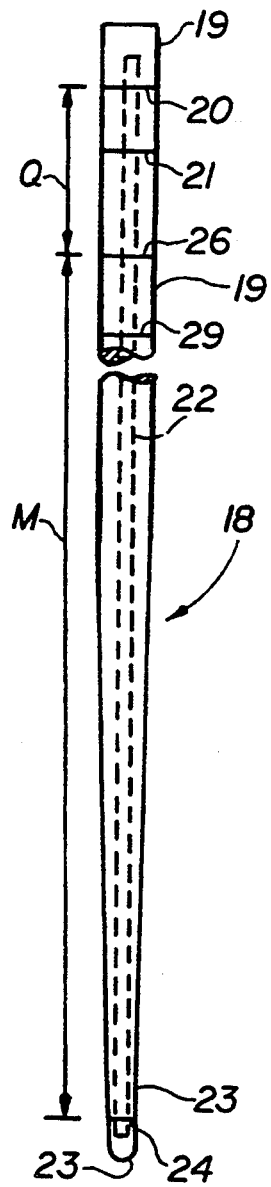
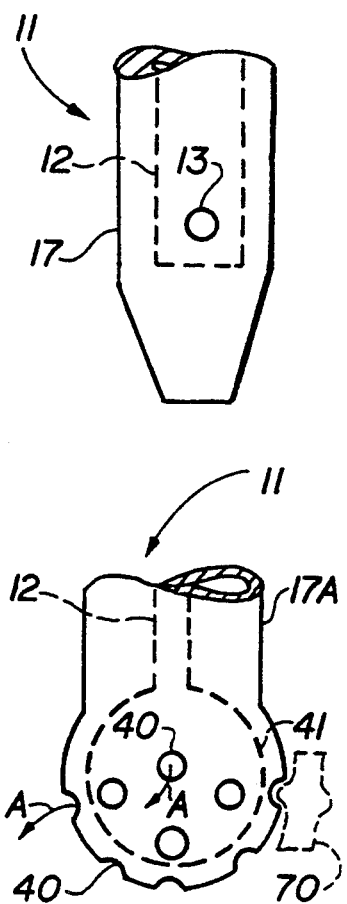
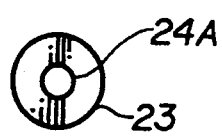
FIG. 1  FIG. 2  FIG. 3  FIG. 5  FIG. 2A

METHOD FOR TESTING FOR ESOPHAGITIS

BACKGROUND OF THE INVENTION

This invention relates to a method and apparatus for diagnosing esophagitis in a patient.

More particularly, the invention relates to portable apparatus of inexpensive manufacture which can quickly and easily be utilized in a hospital emergency room, in a physician's office, or at the residence of a patient to determine whether chest pains experienced by the patient are, instead of being caused by a heart condition, caused by esophagitis.

In another respect, the invention relates to esophagitis test apparatus which administers a test fluid to a patient under atmospheric pressure and the force of gravity and utilizes displacement pressures generated by peristaltic motion to assist in the distribution of the fluid in the esophagus of a patient.

As noted at page 54 in the February 1983 issue of the journal *Hospital Practice*:

"Next to abdominal pain, chest pain poses the most challenging differential diagnosis to the medical acumen of clinicians, who—rather than examine the patient at home, or even in the office, and face dependence on their clinical skills alone—now are prone to refer patients directly to the hospital emergency room. Once there, it is all too difficult to avoid the increasingly expensive technological "rule-out routine" in the face of medical, legal, and peer pressures for prompt decisions. A characteristic description of strangling retrosternal pain, accompanied by mortal anxiety and related to exertion, is new so habitually associated with coronary artery disease that angina due to other causes, such as pericarditis or esophagitis, are put on the far-back burner even in patients in low-risk coronary disease categories. As an interested student for many years of anterior chest pain of non-coronary disease origin, I was intrigued with a report from Ipswich, England, of 100 unselected consecutive emergency patients with anterior chest pain who were followed to their final diagnosis to discover, specifically, the prevalence of esophageal disease as a cause of their symptom. One fifth (16) of the 77 patients whose pain was definitely considered "anginal" had abnormalities of the esophagus demonstrated by endoscopy with biopsy, manometry, radiology, and acid perfusion (Bernstein and Baker method). None of these 16 had abnormal exercise tolerance tests. In eight a proactive test reproduced the symptoms. Esophageal acid perfusion was the most useful investigation in this group. However, in the remaining eight patients, testing reveal esophageal abnormalities that were not associated with pain at all. The authors conclude that the esophagus must be investigated in all patients with cardiac-like chest pain but apparently normal hearts, even when there is no overt sign of esophageal dysfunction, such as heartburn or dysphagia."

The editor in the above referenced February 1983 issue of Hospital Practice noted:

"What is badly needed, therefore, is a simple, safe esophageal maneuver that turns on chest pain and has a high degree of sensitivity."

It would therefore be highly desirable to provide an improved method for testing for esophagitis patients who are experiencing chest pain.

SUMMARY OF THE INVENTION

It is a principal method of the invention to provide an improved method for determining the presence of esophagitis in a patient experiencing chest pain.

A further object of the invention is to provide an improved esophagitis test method which is simple in execution and can be readily and quickly utilized in a hospital emergency room, in a physician's office, or at the home of a patient.

Another object of the invention is to provide an improved esophagitis test method which requires an unusually small amount of portable equipment which can be carried on the person of or in the treatment bag of a physician.

Still a further object of the invention is to provide an improved esophagitis test apparatus which automatically dispenses a test fluid into the distal esophagus of a patient under atmospheric pressure and the force of gravity.

Yet another object of the invention is to provide an improved esophagitis test apparatus which is shaped and dimensioned to utilize peristalsis of the esophagus to administer a test fluid in the esophagus and to indicate whether the peristaltic function of the esophagus is normal or is in stasis.

These and other, further and more specific objects and advantages of the invention will be apparent to those skilled in the art from the following detailed description thereof, taken in conjunction with the drawings, in which:

BRIEF DESCRIPTION OF THE DRAWINGS

FIG. 1 is a front elevation view illustrating apparatus constructed in accordance with the invention to test a patient to determine whether the patient is suffering from esophagitis;

FIG. 2 is a front elevation view illustrating apparatus constructed in accordance with an alternate embodiment of the invention for diagnosing esophagitis;

FIG. 2A is a bottom view illustrating the aperture in the tip of the apparatus of FIG. 2 after the aperture has been unsealed;

FIG. 3 is an enlarged view of the tip of the apparatus of FIG. 1 illustrating further construction details thereof;

DESCRIPTION OF THE PREFERRED EMBODIMENTS

Figure 4:
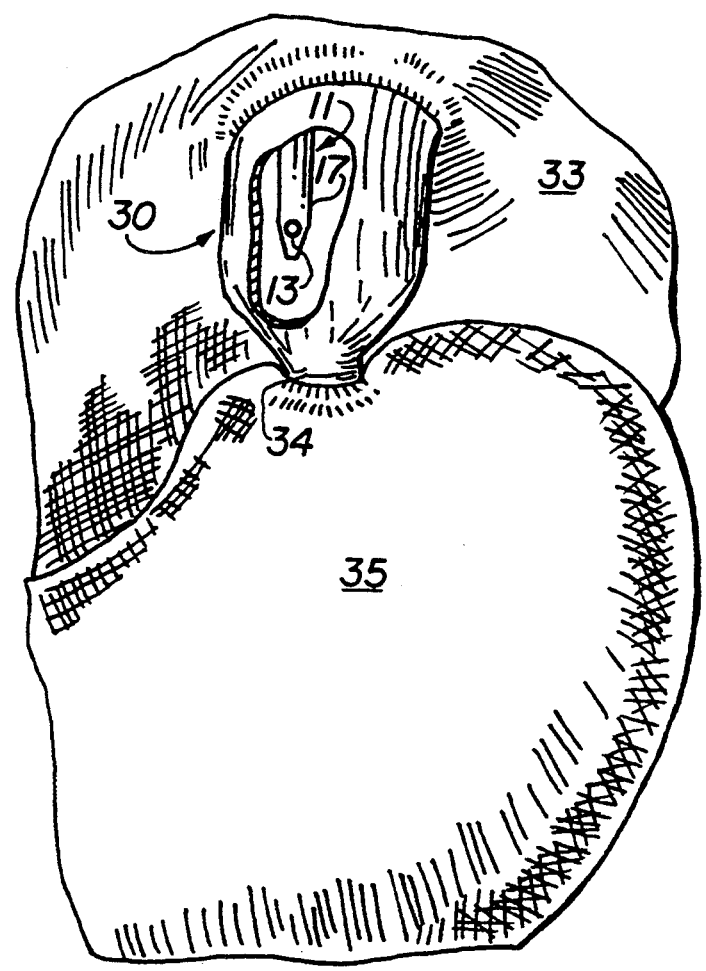
FIG. 4 is a view of the stomach and distal end of the esophagus illustrating the apparatus of FIG. 1 inserted in the esophagus; and, FIG. 5 is a side view of an alternate embodiment of a fluid dispensing tip designed to enhance the effect of peristalsis in causing fluid to flow outwardly through the tip into the esophagus.

Briefly, in accordance with my invention, I provide apparatus for insertion into the esophagus through the mouth or nose to test for esophagitis in a patient. The apparatus comprises a sealed elongate pliable reservoir having at least one wall, a lower end for insertion through the nose or mouth into the end of the esophagus adjacent the stomach, and an upper end to extend out of the nose or mouth after the first end is inserted into the end of the esophagus; a 0.05 to 0.5N aqueous solution of hydrochloric acid; at least a first sealed aperture formed in the lower end; and, at least a second sealed aperture formed in the upper end. The first aperture and the lower end are shaped and dimensioned such that when the first and second apertures are unsealed, the aqueous solution drips through the fist aperture under the force of gravity, under atmospheric pressure, and under peristaltic action; when the first aperture is unsealed and the lower end is inserted in the esophagus, peristalsis of the esophagus causes the walls of the esophagus to contact the first end and generate forces which act to draw fluid out of the first aperture into the esophagus; and, when the first aperture is unsealed and the second aperture remains sealed, the aqueous solution remains in the reservoir and does not flow through the first aperture.

In accordance with another embodiment of my invention, I provide a method of administering a test to a patient to detect the condition of esophagitis in the patient. The method includes the steps of charging a tube with a solution of hydrochloric acid. The tube has pliable walls, upper and lower ends, at least a first aperture formed in the lower end, and at least a second aperture formed in the upper end. The tube is shaped and dimensioned such that the lower end can be inserted through the nose of a patient and into the lower portion of the esophagus adjacent the stomach, and such that after the first end is inserted through the nose or mouth into the lower portion of the esophagus adjacent the stomach, the upper end extends outwardly from the nose and can be grasped. The first aperture is shaped and dimensioned such that when the first and second apertures are open the solution drips through the first aperture under atmospheric pressure and the force of gravity and when the first aperture is open and the second aperture is closed, the solution remains in the tube and does not flow through the first aperture. After the tube is charged with a solution of hydrochloric acid, the second aperture is closed, the lower end is inserted through the nose of a patient into the lower portion of the esophagus adjacent the stomach, and, the second aperture is unsealed to permit the solution to drip through the first aperture under the force of gravity into the lower portion of the patient's esophagus.

In still another embodiment of my invention, I provide apparatus for insertion into the esophagus through the mouth or nose to test for esophagitis in a patient. The apparatus comprises an elongate pliable reservoir having at least one wall, a lower end for insertion through the nose of mouth into the end of the esophagus adjacent the stomach, and an upper end to extend out of the nose or mouth after the first end is inserted into the end of the esophagus; a liquid solution in the reservoir and effective to irritate the burned lining of the esophagus when the patient has esophagitis; a first aperture formed in the lower end; and, a second sealed aperture formed in the upper end. The first aperture is shaped and dimensioned such that when the second aperture is unsealed, the liquid solution drips through the first aperture under atmospheric pressure and the force of gravity and, when the second aperture is sealed, the liquid solution remains in the reservoir and does not flow through the first aperture. The second aperture can be unsealed by cutting off a portion of the upper end of the reservoir. The reservoir can have a length equal to or less than 40 centimeters when the upper end is cut off.

Turning now to the drawings, which depict the presently preferred embodiments of the invention for the purpose of illustrating the practice thereof and not by way of limitation of the scope of the invention, and in which like reference characters refer to corresponding elements throughout the several views, FIG. 1 illustrates apparatus constructed in accordance with the invention and including an elongate pliable reservoir or tube 11 having liquid impermeable cylindrical walls, a lower end 17 for insertion through the nose or mouth into the end of the esophagus adjacent the stomach, and an upper end 16 which extends out of the nose or mouth after the lower end 17 is inserted into the end of the esophagus. Cap 28 on end 16 is sized to prevent cap 28 from passing into the nose and/or mouth of a patient. The reservoir 12 ordinarily is charged with and stores one-half to twenty-five, preferably five to fifteen, milliliters of a 0.05 to 0.5N, preferably 0.08 to 0.2N, solution of hydrochloric or some other desired acid. Any desired volume of solution, however, can be stored in reservoir 12. Reservoir 12 is completely sealed or enclosed by tube 11 except for aperture 13 formed through end 17 of tube 11. Aperture 13 is normally covered by a circular removable seal (not shown). The circular seal can, for example, be similar to a circular band aid. The adhesive on the back of the circular seal secures the seal to end 17 and prevents aqueous solution from flowing out through aperture 13. When the apparatus is to be used by inserting end 17 through the nose into the esophagus of a patient, the circular seal over aperture 13 is removed, and, the apparatus of FIG. 1 is cut along line 14 to remove cap 28 and a portion of end 16 and expose and unseal the upper circular end or aperture of cylindrical reservoir 12. The apparatus of FIG. 1 ordinarily is cut along line 15 to expose and unseal the upper end or aperture of cylindrical reservoir or hollow 12 after the apparatus is inserted through the mouth of a patient.

The length, indicated by arrows L in FIG. 1, from scribed line 25 to aperture 13 is equal to or less than 45 to 47 centimeters so that when end 17 is inserted through the nose into the esophagus aperture 13 is in the lower end of the esophagus and does not extend into the stomach of the patient. The distance between lines 14 and 25 is indicated by arrows P and is presently five to six centimeters so that end 16 extends out of the nose of the patient when line 25 is held adjacent the entrance to the nose and end 17 is properly positioned in the lower end of the esophagus of the patient. In order to insure that aperture 13 is properly positioned in the esophagus of the patient, line 25 should be maintained in fixed position at the entrance to the nose of the patient.

The length, indicated by arrows N in FIG. 1, from scribed line 27 to aperture 13 is equal to or less than 40 centimeters so that when end 17 is inserted through the mouth into the esophagus of a patient and scribed line 27 is held in fixed position adjacent the lips of the patient aperture 13 is in the lower end of the esophagus and does not extend into the stomach of the patient. The distance between lines 15 and 27 is indicated by arrows O and is five to six centimeters so that end extends out of the mouth of the patient when line 27 is held adjacent the lips of the mouth and end 17 is properly positioned in the lower end of the esophagus of the patient. Line 27 identifies the portion of tube 11 which is held adjacent the lip of the mouth of the patient after end 13 is inserted through the mouth and into the patient's esophagus. It is presently preferred, but not required, that the distance between lines 14 and 25 and between lines 15 and 27 should be a selected distance sufficient for a physician or other user to comfortably grasp and hold end 16 after end 17 is inserted into position in the lower or distal end of the esophagus.

FIG. 3 is an enlarged view of the lower end 17 of tube 11 further illustrating the aperture 13 through which the acid solution in reservoir 12 flows out of tube 11. Aperture 13 is sized such that when the circular adhesive seal is removed from aperture 13 fluid will not flow outwardly through aperture 13 until a portion of end 16 is removed by cutting along line 14 or along line 15 to unseal or open the upper end of reservoir 12. Once a portion of end 16 is cut off along line 14 or line 15, atmospheric pressure and the force of gravity cause solution to drip or flow out through aperture 13. Aperture 13 is presently, but not necessarily, sized such that the solution in reservoir 12 will substantially completely drain out through aperture 13 (after a portion of end 16 is clipped off along line 14 or line 15) within five seconds to five minutes, preferably fifteen seconds to three minutes. Constructing tube 11 to drain five to fifteen milliliters of 0.1N hydrochloric acid solution out of reservoir 12 within fifteen to thirty seconds make the apparatus particularly desirable in use because the tube 11 can be utilized as a simple, quick means for testing for esophagitis. While the time required for the solution in reservoir 12 to drain out can, however, be varied as desired, the rapid discharge of solution out of reservoir 12 in fifteen to thirty seconds is very desirable in emergency room situations.

FIG. 2 illustrates apparatus constructed in accordance with an alternate embodiment of the invention and including a fully sealed elongate pliable reservoir or tube 18 having a liquid impermeable cylindrical wall, a lower end 23 for insertion through the nose or mouth into the end of the esophagus adjacent the stomach, and an upper end 19 which extends out of the nose or mouth after the lower end 17 is inserted into the end of the esophagus. End 19 is larger than end 23 and is sized to prevent end 19 from passing into the nose and/or mouth of a patient. The reservoir 22 is presently charged with and stores one-half to twenty-five, preferably five to fifteen milliliters of a 0.05 to 0.5N, preferably 0.08 to 0.12N, solution of hydrochloric or some other desired acid. Reservoir 22 is completely sealed or enclosed by tube 18. The acidity of the solution can, however, be varied as desired. When tube 18 is to be used by inserting end 23 through the mouth into the esophagus of a patient, tube 18 is cut along line 24 to expose and unseal the lower circular aperture 24A (FIG. 2A) of cylindrical reservoir 22 and, after the tube 18 is inserted through the mouth such that line 29 is held in fixed position at the lips of the mouth and end 23 is positioned in the esophagus, then tube 18 is cut along line 21 to expose and unseal the upper end or aperture of reservoir 22. When the tube 18 is to be inserted through the nose of a patient, tube 18 is cut along line 24 to expose and unseal the lower circular aperture 24A of cylindrical reservoir 22 and, after the tube 18 is inserted through the nose such that line 26 is held in fixed position at the entrance to the nose of the patient and end 23 is position in the esophagus, then tube 18 is cut along line 20 to expose and unseal the upper end or aperture of reservoir 22.

The length, indicated by arrows M in FIG. 2, from scribed line 26 to line 24 is equal to or less than 45 to 47 centimeters so that when end 23 is inserted through the nose into the esophagus, cut end 23 is in the lower end of the esophagus and does not extend into the stomach of the patient. The distance between lines 20 and 26 is indicated by arrows Q and is presently five to six centimeters so that cut end 19 extends out of the nose of the patient when line 26 is adjacent the entrance to the nose and end 23 is properly positioned in the lower end of the esophagus of a patient. Line 26 indicates the portion of tube 18 which should be maintained in position at the entrance to the nose of a patient.

When the tube 18 is inserted through the mouth and cut along line 21 the length from line 29 to line 24 is equal to or less than about forty centimeters. The distance between lines 21 and 29 is five to six centimeters. End 19 extends out of the mouth of the patient when line 29 is held adjacent the lips of the mouth and end 23 is properly positioned in the lower end of the esophagus of the patient. Line 29 therefore indicates the portion of tube 18 which should be held in position adjacent the lips of the mouth of a patient after end 23 is inserted through the mouth, and properly positioned in the distal end of the patient's esophagus. It is presently preferred, but not required, that the distance between lines 20 and 26 and between lines 21 and 29 should be a selected distance sufficient for a physician or other user to comfortably grasp and hold end 19 after end 23 is inserted in the lower or distal end of the esophagus.

In tube 11 aperture 13 is formed at the side of tube 11. In tube 18 the aperture which is formed when end 23 is cut and unsealed along line 24 is at the tip or very bottom of tube 18. One or more apertures can be formed in the lower end 17 of tube 11 or end 23 of tube 18. After the seal is removed from aperture 13 and tube 11 is cut along a line 14 or 15 to unseal the upper end 16 of reservoir 12, the acidic solution stored in reservoir 12 flows out through aperture 13 under atmospheric pressure and the force of gravity. Similarly, after tube 18 is cut along line 24 to unseal the lower end 23 of tube 18 and after tube 18 is cut along line 20 or line 21 to unseal and open the upper end 19 of tube 18, the acidic solution stored and retained in reservoir 22 flows out through aperture 24A under atmospheric pressure and the force of gravity.

The lower tips 17 and 23 of tubes 11 and 18 and the apertures formed in the tips for acidic solution to flow into the distal end of the esophagus are preferably, but not necessarily, shaped and dimensioned to enable the peristalsis of the esophagus to assist in causing fluid to flow out of apertures 13 and 24A after tubes 11 and 18 are inserted in the esophagus and each cut through upper ends 16, 19, respectively to permit fluid to flow through apertures 13 and 24A. Peristalsis most effectively assists in removing fluid from tubes 11 and 18 when the inner walls or surfaces of the esophagus undulate and contract over apertures 13 and 24A or at least over the outer surfaces of tube 11 and 18 which are immediately adjacent apertures 13, 24A. For example, peristaltic action of the inner walls of the esophagus causes the inner esophageal walls to travel over the outer surface of tip 17 (or 23), to extend partially into aperture 13, and to "sweep" or displace fluid from the outermost part of aperture 13 and carry the fluid toward the patient's stomach. As the inner esophageal walls 70 (FIG. 5) sweep or move over aperture 13, they repeatedly, due to the wavelike, circular contractions of the esophagus, extend a short distance into aperture 13 and then withdraw from aperture 13. The peristaltic action also, when it displaces fluid from aperture 13 and toward the lesser sphincter, tends to intermittently generate a small suction force over aperture 13 which acts on fluid from reservoir 12 and exerts a pulling force on the fluid in a direction of travel out through aperture 13 into the esophagus. Consequently, forming the tips 17, 23 to facilitate contact of the tips by the inner walls of the esophagus is desired in order to promote the peristaltic drawing or pulling of fluid through apertures 13 and 24A into the esophagus. One advantage of forming the tips 17 and 23 and the fluid dispensing apertures therein so that the flow of fluid through the apertures is assisted by peristalsis is that the failure of the fluid in the tubes 11, 18 to completely empty into the esophagus within a normal expected period of time can indicate stasis of the esophagus and the absence of peristalsis, suggesting an ailment other than esophagitis.

An alternate embodiment 17A of the tip 17 of tube 11 is illustrated in FIG. 5. Tip 17A includes a spherical reservoir 41 which receives acidic aqueous solution flowing from cylindrical reservoir 12. Fluid from reservoir 41 flows outwardly through apertures 40 and into the esophagus in the manner indicated by arrows A in FIG. 5. The spherical shape of the outer surface of tip 17A facilitates contact of the outer surface by the inner walls of the esophagus and, accordingly, facilitates peristalsis of the esophagus causing an increase in the rate of fluid flow through apertures 40. The taper of tube 18 toward tip 23 facilitates the wrapping of the inner walls of the esophagus around tip 23 and therefore facilitates removal of fluid from aperture 24A by peristaltic action.

In use of a tube 11, the seal over aperture 13 is removed and the lower end 17 is inserted through the nose or mouth to position end 17 in the distal esophagus above or prior to the juncture of the esophagus and stomach (FIG. 4). If tube 11 is inserted through the nose, line 25 is placed adjacent and maintained in position at the entrance to the patient's nose and end 16 is cut along line 14 to permit the acidic solution in reservoir 12 to flow out of aperture 13 under atmospheric pressure and the flow of gravity. If tube 11 is inserted through the mouth, line 27 is placed adjacent and maintained in position next to the lips of the patient and end 16 is cut along line 15. Alternatively, for example, end 16 can be cut along line 14 (or 15) and a finger placed over the aperture which defines the upper open end of reservoir 12 and which was exposed and unsealed by so cutting end 16. The finger remains over the aperture until end 17 is properly positioned in the distal end of the esophagus. After end 17 is properly positioned in the esophagus, the finger is removed from the aperture to unseal the aperture and permit the acidic solution in reservoir 12 to flow through aperture 13 under atmospheric pressure, under the force of gravity, and under peristaltic action. In FIG. 5, end 17 of tube 11 is shown positioned in the distal end of esophagus 30 above the lesser sphincter 34 of the esophagus. The distal end of the esophagus 30 extends through the diaphragm 33 to the stomach 35. After a period of time passes during which the acidic solution in reservoir 12 of tube 11 should have completely emptied into the esophagus 30, or after the patient complains of the chest pain, burning sensation or other symptoms which caused the patient to seek medical attention, tube 11 is removed and discarded. Since chest pain or other symptoms associated with esophagitis ordinarily are caused to occur when acid from the stomach contacts the lower part of the esophagus, contacting the esophagus with acidic solution from tube 11 often causes these symptoms to reoccur. As would be appreciated by those of skill in the art, tube 18 is used in a manner similar to that just described for tube 11.

In FIG. 4, for the sake of clarity, the esophagus 30 is illustrated as a hollow, or actual, lumen. In reality, the esophagus is a virtual lumen whose walls will collapse on tube 11 so that the portions of tube 11 which are contacted by the walls of esophagus 30 will be subject to peristaltic action.

In FIG. 1, aperture 13 of tube 11 is, as earlier described, sealed with a removable circular band-aid like seal. The upper apertures of reservoir 12 of tube 11, either the aperture which is exposed when a cut is made through line 14 of end 16 or the aperture which is exposed when a cut is made through line 15 of end 16, are sealed by the cylindrical wall of the upper portion of tube 11. Alternatively, a removable wax plug, a seal which can be punctured with a sharp object, or any other means can be used to seal aperture 13 and the upper apertures of reservoir 12 (or to seal the apertures of tube 18 or any other tube constructed in accordance with the invention) as long as the apertures can be unsealed before and/or during the insertion of the tube 11 in a patient.

Esophagitis is caused when acid from the stomach contacts and burns the lining in the lower part of the esophagus. Once this burn occurs, it can be irritated by the hydrochloric acid solution noted above, or can be irritated by a variety of other known chemical compositions. For example, a bile salt solution or other alkaline solution with a pH greater than about 10 can irritate the burned lining of the esophagus. Alcohol can irritate the burned lining of the esophagus. Consequently, in the practice of the invention, a tube 11 or 18 can be charged with any liquid composition which will flow out of the tube under atmospheric pressure and the force of gravity and which will irritate the burned lining of the esophagus. An aqueous solution of hydrochloric acid is presently preferred because it replicates the hydrochloric acid found in the stomach and also tends to replicate the symptoms which occur in a patient when hydrochloric acid from the stomach contacts the burned lining of the esophagus.

Having described my invention in such terms as to enable those skilled in the art to understand and practice is, and having identified the presently preferred embodiments thereof, I claim:

1. A method of administering a test to a patient to detect the condition of esophagitis in the patient, including the steps of:
   (a) providing a tube having
      (i) at least one pliable wall,
      (ii) first and second sealed ends,
      (iii) a reservoir circumscribed by said wall and extending from said first to said second end, and
      (iv) an acidic aqueous solution stored in said reservoir,
   said tube being shaped and dimensioned such that
      said first end can be inserted through an anatomical opening in the face of a patient and into the end of the esophagus adjacent the stomach,
      after said first end is unsealed and inserted in the esophagus and said second end is unsealed, the peristaltic action of the esophagus generates forces which act to draw fluid through said unsealed first end, and
      after said first end is inserted into the end of the esophagus adjacent the stomach, said second end extends outwardly from the patient's face and can be grasped;

said first end being shaped and dimensioned such that when said first end is unsealed and inserted in the esophagus and said second end is unsealed, said solution flows from said reservoir out through said unsealed first end under atmospheric pressure and the force of gravity, and when said first end is unsealed and inserted in the esophagus and said second end remains sealed, said solution remains in said tube and does not flow from said reservoir out through unsealed first end;

(b) unsealing said first end and inserting said first end of said tube through an anatomical opening in the patient's face and into the lower end of the patient's esophagus adjacent the stomach;

(c) unsealing said second end to permit atmospheric pressure, the force of gravity and peristaltic action to cause said solution to flow through said unsealed first end into the lower end of the patient's esophagus adjacent the stomach; and, (d) monitoring the patient to determine if the patient experiences chest pain or other symptoms associated with esophagitis.

2. The method of claim 1 wherein (a) the anatomical opening comprises the mouth of the patient;

(b) said tube is shaped and dimensioned such that in said first end is inserted through the mouth and into the end of the esophagus adjacent the stomach; and, (c) after said first end is inserted through the mouth into the end of the esophagus adjacent the stomach in step (b), said second end extends outwardly from the mouth and can be grasped.

3. The method of claim 1 wherein (a) the anatomical opening comprises the nose of the patient;

(b) said tube is shaped and dimensioned such that in step (b) said first end is inserted through the nose and into the end of the esophagus adjacent the stomach; and, (c) said second end extends out of the nose after said first end is inserted into the end of the esophagus adjacent the stomach in step (b).

4. A method of administering a test to a patient to detect the condition of esophagitis in the patient, including the steps of (a) providing a tube including (i) at least one wall, (ii) a first sealed end for insertion through an anatomical opening in the patient's face into the end of the esophagus adjacent the stomach, (iii) a reservoir circumscribed by said wall, (iv) a second sealed end, said tube being shaped and dimensioned such that said second end extends outwardly from the patient's face after said first end is inserted through an anatomical opening in the patient's face into the end of the esophagus adjacent the stomach, said reservoir extending from said first to said second end, (v) a liquid solution stored in said reservoir while said first end of said tube is inserted into the esophagus, said solution effective to irritate the burned lining of the esophagus when the patient has esophagitis, said tube being shaped and dimensioned such that when said first end is unsealed and inserted in the esophagus and said second end is unsealed, the force of gravity and atmospheric pressure cause said liquid solution to flow from said reservoir out through said unsealed first end, and when said first end is unsealed and inserted in the esophagus and said second end remains sealed, said liquid solution remains in said reservoir and does not flow from said reservoir out through said unsealed first end;

(b) unsealing and inserting said first end of said tube through an anatomical opening in the patient's face and into the end of the esophagus adjacent the stomach;

(c) unsealing said second end to permit atmospheric pressure, and the force of gravity to cause said solution to flow through said unsealed first end of said tube and into the end of the patient's esophagus adjacent the stomach; and, (d) monitoring the patient to determine if the patient experiences chest pain or other symptoms associated with esophagitis.

5. The method of claim 4 wherein said reservoir is shaped and dimensioned such that in step (c), said liquid solution completely empties from said reservoir through said unsealed first end under the force of gravity and atmospheric pressure in a period of time in the range of from five seconds to five minutes.

6. The method of claim 5 wherein the volume of said liquid solution stored in said reservoir in step (a) is in the range of one-half milliliter to twenty-five milliliters.

7. The method of claim 4 wherein the volume of said liquid solution stored in said reservoir in step (a) is in the range of one-half milliliter to twenty-five milliliters.

* * * * *